United States Patent [19]
Boix-Igleasias et al.

[11] 4,367,232
[45] Jan. 4, 1983

[54] PIPERIDINE DERIVATIVES

[75] Inventors: José Boix-Igleasias; José P. Soto; Armando Vega-Noverola; Robert G. W. Spickett; Jacinto M. Mauri, all of Barcelona, Spain

[73] Assignee: Fordonal, S.A., Madrid, Spain

[21] Appl. No.: 845,958

[22] Filed: Oct. 27, 1977

[30] Foreign Application Priority Data

Oct. 29, 1976 [GB] United Kingdom ............... 45146/76

[51] Int. Cl.$^3$ ................. C07D 211/58; A61K 31/445
[52] U.S. Cl. .................................... 424/267; 546/224
[58] Field of Search ...................... 260/293.77, 293.73; 424/267; 546/224

[56] References Cited

U.S. PATENT DOCUMENTS

| | | | |
|---|---|---|---|
| 2,745,837 | 5/1956 | Papa et al. | 546/216 |
| 3,342,826 | 9/1967 | Miller et al. | 260/293.77 |
| 3,445,573 | 5/1969 | Jucker et al. | 546/224 |
| 3,862,139 | 1/1975 | Podesva et al. | 260/293.77 |
| 3,954,776 | 5/1976 | Muro et al. | 546/194 |
| 3,963,745 | 6/1976 | Cale et al. | 260/326.83 |

FOREIGN PATENT DOCUMENTS 2513136  2/1975  Fed. Rep. of Germany .

Primary Examiner—Norma S. Milestone
Attorney, Agent, or Firm—Morgan, Finnegan, Pine, Foley & Lee

[57] ABSTRACT

This invention relates to new therapeutically useful piperidine derivatives and salts thereof. The invention also relates to processes for their preparation and pharmaceutical compositions containing them.

3 Claims, No Drawings

PIPERIDINE DERIVATIVES

SUMMARY OF THE INVENTION

According to one aspect of our invention, we provide compounds of the formula

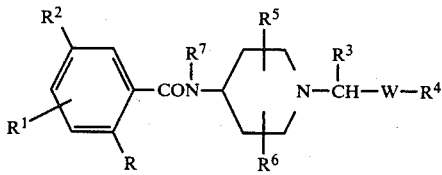

wherein R represents a lower alkoxy or lower alkenyloxy group; $R^1$ and $R^2$, which may be the same or different, each represent a hydrogen or halogen atom, a sulphonamido, amino, lower alkylamino, di(lower)alkylamino, lower alkylsulphonyl or lower alkylsulphonoamido group, or a lower acylamino group in which the acyl moiety is derived from a carboxylic acid (preferably a lower alkanoylamino group), the group represented by the symbol $R^1$ (when other than a hydrogen atom) being in the 3- or 4- position of the phenyl ring, with the proviso that $R^1$ and $R^2$ do not both represent hydrogen atoms; $R^3$ represents a hydrogen atom or a lower alkyl or lower alkenyl group, a cycloalkyl or cycloalkenyl group having from 3 to 7 carbon atoms in the ring, or a phenyl group; $R^4$ represents a cycloalkyl or cycloalkenyl group having from 3 to 7 carbon atoms in the ring, an aroyl (e.g., benzoyl), aryl (e.g., phenyl or naphthyl) or heterocyclyl (e.g., thienyl, pyridyl or pyrimidinyl) group; $R^5$, $R^6$ and $R^7$ each represent a hydrogen atom, a lower alkyl, a lower alkenyl or a benzyl group, with the proviso that $R^5$, $R^6$ and $R^7$ cannot simultaneously represent hydrogen atoms; and W represents a single bond or a lower alkylene (e.g., —CH$_2$— or —CH$_2$—CH$_2$—) or lower alkenylene (e.g., —CH:CH—) group, and pharmacogocially-acceptable acid addition salts, quaternary ammonium derivatives or N-oxide derivatives thereof.

The aryl group represented by $R^4$ may be a phenyl group of the general formula

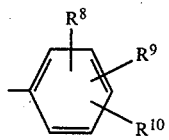

wherein $R^8$, $R^9$ and $R^{10}$ each represent a hydrogen or halogen atom or a lower alkoxy, hydroxy, nitro, amino, lower alkylamino, lower dialkylamino, trifluoromethyl or lower alkyl group, or $R^8$ and $R^9$ together may form a methylenedioxy group in which case $R^{10}$ represents a hydrogen atom.

The qualification "lower" as applied herein to alkoxy, alkenyloxy, alkyl, acyl, alkanoyl, alkenyl, alkylene, and alkenylene groups means that the group in question contains at most 6 carbon atoms.

Preferred compounds of general formula I are those of the more specific formula

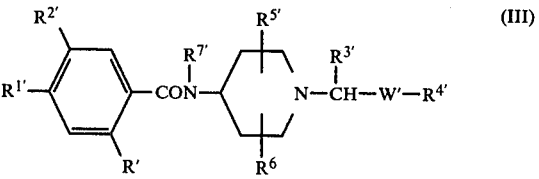

wherein R' represents a lower alkoxy (preferably methoxy or ethoxy) or allyloxy group; $R^{1'}$ represents a hydrogen atom or an amino, lower alkylamino (preferably methylamino) or lower acylamino in which the acyl moiety is derived from a carboxylic acid (preferably lower alkanoylamino, e.g., acetamido or trifluoroacetamido) group; $R^{2'}$ represents a hydrogen or halogen (preferably chlorine or bromine) atom or an amino, sulphonamido or lower alkylsulphonyl (preferably methylsulphonyl) group with the proviso that $R^{1'}$ and $R^{2'}$ do not both represent hydrogen atoms; $R^{3'}$ represents a hydrogen atom, a lower alkyl (preferably methyl) or a phenyl group; $R^{4'}$ represents a cyclohexyl, cyclohexenyl or cyclohexadienyl group or a phenyl group optionally substituted by a halogen atom or a lower alkyl group, or $R^{4'}$ represents a thienyl group, $R^{5'}$ represents a hydrogen atom or a lower alkyl (preferably methyl) group; $R^{6'}$ and $R^{7'}$ each represent a hydrogen atom or a lower alkyl (preferably methyl or ethyl) or benzyl group with the proviso that $R^{6'}$ and $R^{7'}$ are not both hydrogen atoms when $R^{5'}$ represents a hydrogen atom, and W' represents a methylene group or, preferably, a single bond, and pharmaceutically-acceptable acid addition salts thereof.

Of the compounds of general formula III those wherein R' represents a methoxy group, $R^{1'}$ represents an amino group, $R^{2'}$ represents a chlorine atom, $R^{3'}$ represents a hydrogen atom, $R^{4'}$ represents the cyclohexyl, cyclohex-3-enyl or cyclohexa-1,4-dienyl group, or a phenyl group optionally substituted by a halogen atom or a lower alkyl group, $R^{5'}$ represents a hydrogen atom or a methyl group, $R^{6'}$ and $R^{7'}$ each represent a hydrogen atom or a methyl, ethyl or benzyl group with the proviso that $R^{6'}$ and $R^{7'}$ are not both hydrogen atoms when $R^{5'}$ represents a hydrogen atom, and W' represents a single bond, are of particular importance.

Of outstanding importance are N-(1-benzyl-2,6-dimethylpiperid-4-yl)-2-methoxy-4-amino-5-chlorobenzamide, N-(1-benzyl-3-methyl-piperid-4-yl)-2-methoxy-4-amino-5-chlorobenzamide N-ethyl-N-(1-benzylpiperid-4-yl)-2-methoxy-4-amino-5-chlorobenzamide, N-(1-cyclohexylmethyl-3-methylpiperid-4-yl)-2-methoxy-4-amino-5-chlorobenzamide and their pharmaceutically-acceptable addition salts.

As a further aspect of our invention, we provide pharmaceutical compositions comprising compounds of the general formulas I and III together with a pharmaceutically acceptable carrier or diluent.

DETAILED DESCRIPTION OF THE INVENTION

Preparation of Compounds

The compounds of general formula I are prepared by the process which comprises reacting a reactive derivative of a benzoic acid of general formula

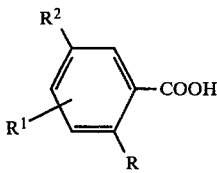

(IV)

wherein R, R¹ and R² are as hereinbefore defined, with a piperidine derivative of the general formula

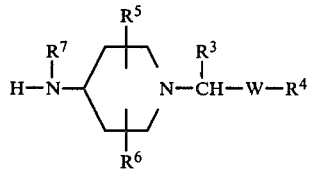

(V)

wherein R³, R⁴, R⁵, R⁶, R⁷ and W are as hereinbefore defined. The reactive derivative of the said benzoic acid may be a halide (preferably chloride), an alkyl ester (preferably methyl ester), an anhydride or a mixed anhydride.

The reaction is preferably carried out in in the presence of an inert organic solvent, such as, for example, ethyl methyl ketone, benzene, toluene, chloroform, tetrahydrofuran, N,N-dimethylformamide, or dioxan, at a temperature between about −5° and about 120° C.

The piperidine derivatives of general formula V in which R⁷ is a hydrogen atom can be prepared by reduction of corresponding 4-piperidone oximes with lithium aluminum hydride in the presence of diethyl ether or tetrahydrofuran, or by reductive amination of corresponding 4-piperidones dissolved in an organic solvent, e.g., an alcohol containing 1 to 4 carbon atoms, in the presence of platinum or Raney nickel as catalyst. The piperidine derivatives of general formula V wherein R³ and/or R⁴ represent a cyclohexadienyl group can be prepared from the corresponding compounds of general formula V wherein R³ and/or R⁴ represent a phenyl group by reduction with lithium in liquid ammonia or a lower alkylamine. The piperidine derivatives of general formual V wherein R⁷ is a lower alkyl, a lower alkenyl, or a benzyl group can be prepared from the corresponding N-acyl substituted compounds by reduction of the carbonyl group therein to methylene using lithium aluminum hydride. Other piperidine derivatives of general formula V can be prepared by methods known per se.

Halides of the benzoic acids of general formula IV can be prepared by reaction of the acid with thionyl chloride or a phosphorus halide in the presence of an inert organic solvent such as benzene, toluene or a halogenated hydrocarbon. Mixed anhydrides of the benzoic acids of general formula IV can be prepared by the reaction of the acid with, for example, an alkyl chloroformate in the presence of an organic nitrogen-containing base, e.g., triethylamine, in an inert organic solvent, e.g., tetrahydrofuran, methylene chloride or N,N-dimethylformamide, and at a temperature between about −20° and about 25° C. Esters and anhydrides of the benzoic acids of formula IV, which may be employed as starting materials in the aforementioned process, can be prepared from the benzoic acids by methods known per se.

The piperidine derivatives of general formula I are also prepared, according to a further feature of the invention, by the direct reaction of a benzoic acid of general formula IV with a piperidine derivative of general formula V in the presence of an appropriate dehydrating agent. Such agents are silicon tetrachloride, a mono-, di- or trialkyl-silyl chloride, titanium tetrachloride, N,N'-dicyclohexyl-carbodiimide, thionyl chloride, sulphur trioxide in dimethyl sulphoxide, toluene-p-sulphonyl chloride, acetone dimethyl acetal or a polymeric dehydrating agent. The reaction is carried out in an inert organic solvent, e.g., methylene chloride, acetone, pyridine, ethyl acetate or dioxan, at a temperature between about 20° and about 110° C.

In the preparation of those compounds of general formula I wherein R¹ and/or R² represent an amino group, by the aforementioned processes, it is sometimes advisable to use as starting material corresponding compounds in which the amino group is protected by an acyl group, the acyl protecting group preferably being acetyl, chloroacetyl, trifluoroacetyl, or phthaloyl. After the reaction the N-acylated intermediate products are subjected to acid or alkaline hydrolysis to give the corresponding compound of general formula I in which R¹ and/or R² represent an amino group. Acid hydrolysis of the N-acylated intermediate compounds may be carried out by heating with dilute hydrochloric acid, preferably at the boiling point of the reaction mixture, while alkaline hydrolysis is preferably carried out at a temperature between about 20° and about 90° C. with sodium or potassium hydroxide in an aqueous-alcoholic solution.

Therapeutic Properties and Administration

The piperidine derivatives of general formula I have as their principal pharmacological properties the ability to antagonise the effects of dopamine or dopaminergic agents or endogenous or exogenous origin and to cause stimulation of serotoninergic mechanisms. In those circumstances where hemeostatic control is a balance between dopaminergic and serotoniergic mechanisms these two actions are synergistic and the precise contribution of each one to the final biological response is difficult to determine. As a group they have exhibited activities which may be considered beneficial in the treatment of obesity and a variety of gastrointestinal and cerebral malfunctions in mammals, including man. Their characteristic properties in experimental animals are antagonism of the effects of dopaminergic agents such as apomorphine, induction of catatonia, production of local anaesthesia, stimulation of gastrointestinal transit, and induction of both spasmogenic and spasmolytic effects on smooth muscle according to the initial resting tone. Nevertheless, as within the series antidopaminergic, serotoninergic and local anaesthetic potency do not necessarily run in parallel, the clinical applications of the various derivatives may well be different. As a group, they may be useful as anorectic drugs in the treatment of obesity, and be effective in the treatment of nausea and vomiting of diverse origin such as that resulting from gastrointestinal disorders, congestive heart failure, post-operative conditions, etc., as well as in the treatment of other gastrointestinal disorders such as dyspepsia, flatulance, bile regurgitation, hiatus hernia, peptic ulcer, reflux oesophagitis, gastritis, duodenitis and cholelithiasis. They may also be useful in the treatment of a variety of conditions affecting the central nervous system such as acute and chronic psychosis, manic psychosis, schizophrenias, serious disturbances of behavior, non-melancholic depressive states and migraine. Useful anoretic and antiemetic dosages of the more interesting compounds appear to lie between about 5 and about 100 mg per day.

For therapeutic purposes the compounds of general formula I may be employed in the form of non-toxic, biologically and pharmacologically-acceptable inorganic or organic acid addition salts such as sulphates, hydrohalides, phosphates, lower alkanesulphonates, arylsulphonates, and salts of aliphatic or aromatic acids of from 1 to 20 carbon atoms which may contain one or more double bonds, or other functional groups such as hydroxy, lower alkoxy, amino, or keto, e.g. fumarates.

They may also be employed in the form of pharamacologically-acceptable quaternary ammonium salts such as those salts formed by reaction of the compounds of general formula I with lower alkyl halides (e.g., methyl iodide) or sulphates, or in the form of oxygenated derivatives in which oxygen is attached to the nitrogen atom of the piperidine nucleus, viz., the N-oxides.

The pharmacologically-acceptable acid addition salts, quaternary ammonium salts and N-oxides of the compounds of general formula I may be prepared by methods known per se.

Also included within the scope of the present invention are pharmaceutical compositions which comprise, as active ingredient, at least one compound of general formula I or a pharmocologically-acceptable acid addition salt, quaternary ammonium derivative, or N-oxide thereof, in association with a pharmaceutically-acceptable carrier or diluent. Preferably the compositions are made up in a form suitable for oral, topical, percutaneous, or parenteral administration.

The pharmaceutically-acceptable carriers or diluents which are admixed with the active compound, or compounds, or salts of such compounds, to form the compositions of this invention are well known per se and the actual excipients used depend, inter alia, on the intended method of administering the compositions. Compositions of this invention are preferably adapted for administration per os. In this case, the compositions for oral administration may take the form of tablets, capsules, lozenges, or effervescent granules or liquid preparations, such as mixtures, elixirs, syrups or suspensions, all containing one or more compounds of the invention; such preparations may be made by methods well known in the art.

The diluents which may be used in the preparations of the compositions include those liquid and solid diluents which are compatible with the active ingredient, together with coloring or flavoring agents if desired. Tablets or capsules may conveniently contain between about 1 and about 200 mg, and preferably from about 2 to about 100 mg, of active ingredient or the equivalent amount of an acid addition salt, quaternary ammonium derivative or N-oxide thereof.

The liquid compositions adapted for oral use may be in the form of solutions or suspensions. The solutions may be aqueous solutions of a soluble salt or other derivative of the active compound in association with, for example, sucrose to form a syrup. The suspensions may comprise an insoluble active compound of the invention or acid addition salt or quaternary ammonium derivative thereof in association with water, together with a suspending agent or flavoring agent.

Compositions for parenteral injection may be prepared from soluble salts, which may or may not be freeze-dried and which may be dissolved in water or an appropriate parental injection fluid.

In another aspect of the invention, the compounds, may be mixed with other active anti-acid and anti-ulcer agents (excluding anticholinergic agents) for oral or, in appropriate cases, for parenteral use.

Standard pharmaceutical tests have been run with mice and rats using compounds of this invention. The instant compounds have been compared with Clebopride hydrochloride, i.e., N-(1-benzylpiperid-4-yl)-2-methoxy-4-amino-5-chlorobenzamide hydrochloride, which is disclosed in co-pending U.S. patent application Ser. No. 558,908 filed Mar. 17, 1975, incorporated herein by reference.

As can be seen from Table 1, while some of the compounds of this invention compare with Clebopride hydrochloride with respect to anorexia and stomach-emptying, each of the compounds of the present invention is more effective with respect to anti-apomorphine activity.

TABLE 1

PHARMACOLOGICAL ACTIVITY OF SOME COMPOUND OF FORMULA III DEMONSTRATING THE APPEARANCE OF QUALITATIVELY DIFFERENT PROFILES

| R' | R1' | R2' | R3' | R4' | R5' | R6' | R7' | W' | Anti-apo-morphine[b] | Anorexia[c] | Stomach emptying[d] |
|---|---|---|---|---|---|---|---|---|---|---|---|
| [a]MeO | NH$_2$ | Cl | H | phenyl | H | H | H | — | 2.5 | 84% | +++ |
| " | " | " | CH$_3$ | " | " | " | CH$_3$ | — | >300 | 0 | 0 |
| " | " | " | H | " | " | " | " | — | >300 | 0 | + |
| " | " | " | " | " | " | " | C$_2$H$_5$ | — | ≈300 | 0 | + |
| " | " | " | " | " | 3-Me | " | H | — | 58 | 34 | + |
| " | " | " | " | " | 2-Me | 6-Me | " | — | ≈100 | 89 | +++ |

[a]Reference standard (Clebopride hydrochloride)
[b]Approximate oral ED$_{50}$ value for inhibition of apomorphine-induced gnawing behaviour in the rat.
[c]Percentage inhibition of food intake (spaghetti) in screening test at 10 mg kg$^{-1}$ p.os. in the mouse.
[d]Active at 0.3 (+++), 1.0 (++) or 3.0 (+) mg kg$^{-1}$ i.p. in causing significant stomach emptying in the rat.

The following examples illustrate the invention, including preparation of piperidine derivatives and pharmaceutical compositions.

EXAMPLE 1

A solution of 2-methoxy-4-trifluoroacetylamino-5-chlorobenzoyl chloride (17.4 g; 0.055 moles) dissolved in anhydrous ethyl methyl ketone (75 ml) was added little by little to another solution of 1-benzyl-4-ethylamino-piperidine (10.9 g; 0.05 moles) and triethylamine (7.0 ml; 0.05 moles) in anhydrous ethyl methyl ketone (75 ml) at room temperature. On completion of the addition, the mixture was left at room temperature and stirred for 48 hours, and then the mixture was concentrated at reduced pressure, poured into water, and extracted with chloroform. The organic solution was dried (Na$_2$SO$_4$) and the solvent removed in vacuo. The residue was recrystallized from a mixture of methanol and diethyl ether to give N-ethyl-N-(1-benzylpiperid-4- yl)-2-methoxy-4-trifluoroacetylamino-5-chlorobenzamide (17 g), m.p. 198°–200° C.

Also prepared in a similar manner, using appropriate starting materials, were the following:
(a) N-methyl-N-(1-benzylpiperid-4-yl)-2-methoxy-4-trifluoroacetylamino-5-chlorobenzamide, the hydrochloride of which melts at 251°–252° C.;
(b) N-methyl-N-(1-benzylpiperid-4-yl)-2-methoxy-4-acetamido-5-chlorobenzamide, the fumarate of which melts at 199°–201° C. (dec.);
(c) N-methyl-N-(1-benzylpiperid-4-yl)-2-methoxy-5-chlorobenzamide, the fumarate of which melts at 192°–194° C.;
(d) N-benzyl-N-(1-benzylpiperid-4-yl)-2-methoxy-5-chlorobenzamide, the fumarate of which melts at 196°–197° C.;
(e) N-methyl-N-(1-cyclohexa-1',4'-dienylemthylpiperid-4-yl)-2-methoxy-4-acetamide-5-chlorobenzamide, m.p. 147°–149° C.;
(f) N-methyl-N-(1-cyclohexa-1',4'-dienylmethylpiperid-4-yl)-2-methoxy-4-trifluoroacetylamino-5-chlorobenzamide, the hydrochloride of which melts at 210°–212° C.; and
(g) N-methyl-N-(1-cyclohexylmethylpiperid-4-yl)-2-methoxy-4-acetamido-5-chlorobenzamide, the hydrochloride of which melts at 264°–266° C.

The hydrochlorides mentioned above were obtained by addition of a saturated ethanolic solution of hydrogen chloride to a solution of the base in ethanol and further recrystallization.

In a similar manner, the fumarates mentioned above were obtained, by adding fumaric acid in stochiometric amount to a hot ethanolic solution of the piperidine base. The resulting hot solution was cooled and the fumarate crystallized.

EXAMPLE 2

A solution of N-methyl-N-(1-benzylpiperid-4-yl)-2-methoxy-4-trifluoroacetylamino-5-chlorobenzamide (9.6 g; 0.02 moles), prepared as described in Example 1, in methanol (50 ml), water (50 ml) and 8 N sodium hydroxide aqueous solution (50 ml), was stirred for 48 hours at room temperature. Then the mixture was diluted with water, extracted with chloroform, the organic solution dried ($Na_2SO_4$) and the solvent removed in vacuo. The residue (a viscous liquid) was treated with a saturated solution of ethanolic hydrogen chloride and N-methyl-N-(1-benzylpiperid-4-yl)-2-methoxy-4-amino-5-chlorobenzamide hydrochloride (4.8 g); m.p. 259°–260° C. (dec.), was obtained.

Also prepared in a similar manner was N-ethyl-N-(1-benzylpiperid-4-yl)-2-methoxy-4-amino-5-chlorobenzamide hydrochloride, m.p. 243°–245° C.

EXAMPLE 3

Triethylamine (2.78 ml; 0.02 moles) and ethyl chloroformate (1.9 ml; 0.02 moles) were added successively to a stirred suspension of 2-methoxy-4-amino-5-chlorobenzoic acid (4.0 g; 0.02 moles) in anhydrous tetrahydrofuran (150 ml) whilst maintaining the temperature between −5° and −10° C. After stirring at this temperature for half an hour, a solution of 1-cyclohexylmethyl-3-methyl-4-aminopiperidine (4.2 g; 0.02 moles) in anhydrous tetrahydrofuran (25 ml) was added and, after stirring for 1 hour at −5° to −10° C., the temperature was allowed overnight to reach room temperature. The solvent of the mixture was removed in vacuo, the residue poured into water, extracted with chloroform and the organic layers washed with water. The chloroformic solution was dried ($Na_2SO_4$) and the solvent removed in vacuo to give N-(1-cyclohexylmethyl-3-methylpiperid-4-yl)-2-methoxy-4-amino-5-chlorobenzamide (3.5 g), m.p. 173°–176° C.

Also prepared in a similar manner were:
(a) N-(1-benzyl-3-methylpiperid-4-yl)-2-methoxy-4-amino-5-chlorobenzamide, the hydrochloride of which melts at 239°–241° C.;
(b) N-(1-benzyl-2,6-dimethylpiperid-4-yl)-2-methoxy-4-amino-5-chlorobenzamide, the fumarate of which melts at 220°–222° C.; and
(c) N-(1-cyclohexa-1',4'-dienylmethyl-3-methylpiperid-4-yl)-2-methoxy-5-sulphonamidobenzamide, the fumarate of which melts at 207°–209° C. (dec.).

EXAMPLE 4

Triethylamine (4.2 ml; 0.03 moles) and a solution of ethyl chloroformate (2.85 ml; 0.03 moles) in anhydrous tetrahydrofuran (35 ml) were added successively to a solution of 2-methoxy-4-amino-5-chlorobenzoic acid (6.04 g; 0.03 moles) in N,N-dimethylformamide (225 ml) whilst maintaining the temperature at −10° C. After stirring at this temperature for 2 hours, a solution of 1-cyclohexylmethyl-4-methylaminopiperidine (6.15 g; 0.03 moles) in anhydrous tetrahydrofuran (35 ml) was added, and the temperature was allowed overnight to reach room temperature. The mixture was poured into an aqueous solution of sodium bicarbonate, extracted with chloroform and the organic layers washed with water. The chloroformic solution was dried ($Na_2SO_4$) and the solvent removed in vacuo to give a solid which was recrystallized from a mixture of ethanol and diethyl ether. N-methyl-N-(1-cyclohexylmethylpiperid-4-yl)-2-methoxy-4-amino-5-chlorobenzamide (9.6 g) was obtained.

The fumarate was prepared as described in Example 1 and recrystallized from ethanol, m.p. 207°–209° C. (dec.).

Also prepared in a similar manner were:
(a) N-methyl-N-(1-benzylpiperid-4-yl)-2-methoxy-4-methylamino-5-chlorobenzamide, the fumarate of which melts at 214°–216° C. (dec.);
(b) N-methyl-N-(1-benzylpiperid-4-yl)-2-methoxy-4-aminobenzamide the fumarate of which melts at 228°–230° C. (dec.);
(c) N-methyl-N-(1-benzylpiperid-4-yl)-2-methoxy-4-amino-5-bromobenzamide, the fumarate of which melts at 153°–156° C.;
(d) Bis-[N-methyl-N-(1-benzylpiperid-4-yl)-2-ethoxy-4-amino-5-chlorobenzamide] fumarate, m.p., 214°–216° C.;
(e) N-methyl-N-(1-benzylpiperid-4-yl)-2-allyloxy-4-amino-5-chlorobenzamide, the fumarate of which melts at 215°–217° C. (dec.);
(f) N-methyl-N-(1-benzylpiperid-4-yl)-2-methoxy-5-sulphonamidobenzamide, the fumarate of which melts at 189°–191° C. (dec.);
(g) N-methyl-N-(1-benzylpiperid-4-yl)-2-methoxy-5-methylsulphonylbenzamide, the fumarate of which melts at 197°–199° C. (dec.);
(h) N-methyl-N-(1-p-methylbenzylpiperid-4-yl)-2-methoxy-4-amino-5-chlorobenzamide, the fumarate of which melts at 228°–230° C. (dec.);
(i) N-methyl-N-(1-p-methylbenzylpiperid-4-yl)-2-methoxy-4-amino-5-bromobenzamide, the fumarate of which melts at 220°–222° C. (dec.);

(j) N-methyl-N-(1-p-chlorobenzylpiperid-4-yl)-2-methoxy-4-amino-5-chlorobenzamide, the fumarate of which melts at 235°–237° C. (dec.);

(k) N-methyl-N-(1-p-chlorobenzylpiperid-4-yl)-2-methoxy-4-amino-5-bromobenzamide, the fumarate of which melts at 230°–232° C. (dec.);

(l) N-methyl-N-[1-(1-phenylethyl)piperid-4-yl]-2-methoxy-4-amino-5-chlorobenzamide, the fumarate of which melts at 207°–209° C. (dec.);

(m) N-methyl-N-[1-(1-phenylethyl)piperid-4-yl]-2-methoxy-4-amino 5-bromobenzamide, the fumarate of which melts at 201°–203° C. (dec.);

(n) N-methyl-N-(1-phenethylpiperid-4-yl)-2-methoxy-4-amino-5-chlorobenzamide, the hydrochloride of which melts at 286°–288° C. (dec.);

(o) N-methyl-N-(1-diphenylmethylpiperid-4-yl)-2-methoxy-4-amino-5-chlorobenzamide, m.p. 222°–224° C. (dec.);

(p) N-methyl-N-[1-(2-thienylmethyl)piperid-4-yl]-2-methoxy-4-amino-5-chlorobenzamide, the hydrochloride of which melts at 269°–271° C. (dec.);

(q) N-methyl-N-(1-cyclohexa-1',4'-dienylmethylpiperid-4-yl)-2-methoxy-4-amino-5-chlorobenzamide, the fumarate of which melts at 240°–242° C.;

(r) N-methyl-N-(1-cyclohexa-1',4'-dienylmethylpiperid-4-yl)-2-methoxy-4-amino-5-bromobenzamide, the fumarate of which melts at 233°–235° C. (dec.);

(s) N-methyl-N-(1-cyclohex-3'-enylmethylpiperid-4yl)-2-methoxy-4-amino-5-chlorobenzamide, the fumarate of which melts at 195°–197° C. (dec.);

(t) N-methyl-N-(1-benzylpiperid-4-yl)-2-methoxy-4,5-diaminobenzamide, the fumarate of which melts at 224°–226° C. (dec.); and (u) N-methyl-N-(1-cyclohexa-1',4'-dienylmethylpiperid-4-yl)-2-methoxy-5-methylsulphonylbenzamide, the fumarate of which melts at 184°–186° C. (dec.).

EXAMPLE 5

A mixture of N-methyl-N-(1-benzylpiperid-4-yl)-2-methoxy-4-acetamido-5-chlorbenzamide (12.9 g; 0.03 moles), prepared as described in Example 1, concentrated hydrochloric acid (10 ml) and water (30 ml) was boiled under reflux for 2 hours. The solution was concentrated in vacuo and the residue recrystallized from ethanol. The N-methyl-N-(1-benzylpiperid-4-yl)-2-methoxy-4-amino-5-chloro-benzamide hydrochloride (10.8 g) was obtained, m.p. 259°–260° C. (dec.)

EXAMPLE 6

N,N'-dicyclohexylcarbodiimide (10.3 g; 0.05 moles) and 1-benzyl-4-methylaminopiperidine (10.2 g; 0.05 moles) were added successively to a solution of 2-methoxy-5-chlorobenzoic acid (9.3 g; 0.05 mole) in methylene chloride (250 ml). After stirring overnight at room temperature, the insoluble N,N'-dicyclohexylurea was filtered off, the solution was washed with water, dried (Na$_2$SO$_4$) and the solvent removed in vacuo to give an oil. It was salified with fumaric acid as described in Example 1 to give 10.3 g of N-methyl-N-(1-benzylpiperid-4-yl)-2-methoxy-5-chlorobenzamide fumarate, m.p. 192°–194° C.

EXAMPLE 7

To a solution of N-methyl-N-(1-benzylpiperid-4-yl)-2-methoxy-4-acetamido-5-chlorobenzamide (4.3 g; 0.01 moles), prepared as described in Example 1, in acetone (100 ml), a solution of methyl iodide (2.84 g; 0.02 moles) in acetone (20 ml) was slowly added. The mixture was stirred at room temperature overnight, an additional amount of methyl iodide (2.2 g; 0.016 moles) was added, and then the mixture was boiled under reflux for 3 hours. The mixture was evaporated in vacuo and the residue triturated with diethyl ether to five 5.3 g of N-methyl-N-(1-benzylpiperid-4-yl)-2-methoxy-4-acetamido-5-chloro-benzamide methyl iodide. After washing with acetone and recrystallization from ethanol, this compound melted at 204° C.

EXAMPLE 8

To a solution of N-methyl-N-(1-phenethylpiperid-4-yl)-2-methoxy-4-acetamido-5-chlorobenzamide (3.5 g; 0.0079 moles) [melting point 151°–153° C., prepared according to the procedure of Example 1] in glacial acetic acid (50 ml), a 30% hydrogen peroxide solution (3 ml) was added. The mixture was heated for 12 hours at a temperature between 70° and 80° C., the solvent removed in vacuo and the residue dissolved with chloroform. This solution was washed with saturated aqueous solution of sodium bicarbonate, dried (Na$_2$SO$_4$) and the solvent removed in vacuo. The residue was crystallized from diethyl ether to give 2.6 g of the N'-oxide, m.p. 209°–211° C. (dec.)

The following Examples illustrate pharmaceutical compositions according to the present invention.

EXAMPLE 9

One hundred thousand tablets, each containing 10 mg of N-(1-benzyl-3-methylpiperid-4-yl)-2-methoxy-4-amino-5-chlorobenzamide hydrochloride, were prepared from the following formulation:

| | |
|---|---|
| N—(1-benzyl-3-methylpiperid-4-yl)-2-methoxy-4-amino-5-chlorobenzamide hydrochloride | 1000 g |
| microcrystalline cellulose | 1800 g |
| lactose spray dried | 9020 g |
| carboxymethyl starch | 520 g |
| sodium stearyl fumarate | 80 g |
| colloidal silicon dioxide | 80 g |

Procedure

All the powders were passed through a screen with an opening of 0.6 mm. They were then all mixed in a suitable mixer for 30 minutes and compressed into 125 mg tablets using 6 mm discs and flat bevelled punches. The disintegration time of the tablets was about 60 seconds.

EXAMPLE 10

One hundred thousand capsules, each containing 10 mg of N-(1-benzyl-3-methyl-piperid-4-yl)-2-methoxy-4-amino-5-chlorobenzamide hydrochloride, were prepared from the following formulation:

| | |
|---|---|
| N—(1-benzyl-3-methylpiperid-4-yl)-2-methoxy-4-amino-5-chlorobenzamide hydrochloride | 1000 g |
| lactose | 8100 g |
| sodium lauryl sulphate | 370 g |
| corn starch | 8000 g |
| alpine talc | 530 g |

Procedure

The above ingredients were sieved through a 40 mesh sieve, then mixed in a suitable mixer and distributed into 100,000 gelatine capsules (180 mg).

EXAMPLE 11

Ten thousand suppositories, each containing 15 mg of N-(1-benzyl-3-methylpiperid-4-yl)-2-methxoy-4-amino-5-chlorobenzamide hydrochloride, were prepared as follows:

| | |
|---|---|
| N—(1-benzyl-3-methylpiperid-4-yl)-2-methoxy-4-amino-5-chlorobenzamide hydrochloride | 150 g |
| theobroma oil | 19,850 g |

Procedure

The theobroma oil was melted and the active compound suspended in it. The mixture was then poured into appropriate suppository molds to make 2.0 g suppositories.

EXAMPLE 12

Fifty thousand ampoules, each containing 10 mg of N-(1-benzyl-3-methyl-piperid-4-yl)-2-methxoy-4-amino-5-chlorobenzamide hydrochloride, were prepared from the following formulation:

| | |
|---|---|
| N—(1-benzyl-3-methylpiperid-4-yl)-2-methoxy-4-amino-5-chlorobenzamide hydrochloride | 500 g |
| sodium chloride | 500 |
| water injectable grade q.s. | 100 liters |

Procedure

The N-(1-benzyl-3-methylpiperid-4-yl)-2-methoxy-4-amino-5-chlorobenzamide hydrochloride and the sodium chloride were dissolved in approximately 80 liters of water with slight heating. The solution was diluted with water to 100 liters, passed through a bacteria-retaining filter, and filled into 2 ml glass ampoules in known manner. The production of the injectable solution can take place under sterile conditions. It is also possible to work under normal conditions and then to heat-sterilize the filled ampoules.

EXAMPLE 13

One thousand bottles of 150 ml, each containing 150 mg of N-(1-benzyl-3-methylpiperid-4-yl)-2-methoxy-4-amino-5-chlorobenzamide hydrochloride, were prepared as follows:

| | |
|---|---|
| N—(1-benzyl-3-methylpiperid-4-yl)-2-methoxy-4-amino-5-chlorobenzamide hydrochloride | 150 g |
| sorbitol | 70000 g |
| sorbic acid | 125 g |
| citric acid | 125 g |
| distilled water q.s. | 150 liters |
| flavoring agent | q.s. |

Procedure

The N-(1-benzyl-3-methylpiperid-4-yl)-2-methoxy-4-amino-5-chlorobenzamide hydrochloride and the sorbic acid were dissolved in 100 liters of water, and then the sorbitol, citric acid and flavoring agent were added with stirring until dissolution. The mixture was diluted to 150 liters and divided amongst the bottles.

Similar compositions to those described in Examples 9 to 13 can be prepared having as the active ingredient piperidine derivatives of general formula I other than N-(1-benzyl-3-methylpiperid-4-yl)-2-methoxy-4-amino-5-chlorbenzamide, for example other products conforming to that formula mentioned in Examples 1 to 4, 7 and 8.

We claim:

1. N-(1-Benzyl-2,6-dimethylpiperid-4-yl)-2-methoxy-4-amino-5-chlorobenzamide.

2. A pharmacologically-acceptable N-oxide of, acid addition salt of, or quaternary ammonium salt of the compound of claim 1.

3. a pharmacological composition which comprises, as active ingredient, piperidine derivative as claimed in claim 1, in association with a pharmacologically-acceptable carrier or diluent.

* * * * *